(12) United States Patent
Nichols et al.

(10) Patent No.: US 8,142,482 B2
(45) Date of Patent: Mar. 27, 2012

(54) APPARATUS FOR SECURING A SPINAL ROD SYSTEM

(75) Inventors: David Nichols, Trumbell, CT (US); Eric Finley, San Diego, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1208 days.

(21) Appl. No.: 11/899,503

(22) Filed: Sep. 5, 2007

(65) Prior Publication Data

US 2008/0004629 A1    Jan. 3, 2008

Related U.S. Application Data

(62) Division of application No. 10/441,764, filed on May 20, 2003, now Pat. No. 7,278,995.

(60) Provisional application No. 60/385,994, filed on Jun. 4, 2002.

(51) Int. Cl.
*A61B 17/56* (2006.01)
(52) U.S. Cl. ....................................................... 606/279
(58) Field of Classification Search .................. 606/246, 606/264, 265, 270, 272, 279, 86 R, 99, 104, 606/86 A
See application file for complete search history.

(56) References Cited

U.S. PATENT DOCUMENTS

| 5,707,371 | A  | 1/1998  | Metz-Stavenhagen et al. |
| 5,885,299 | A  | 3/1999  | Winslow et al. |
| 5,946,988 | A  | 9/1999  | Metz-Stavenhagen et al. |
| 6,139,549 | A  | 10/2000 | Keller et al. |
| 6,183,472 | B1 | 2/2001  | Lutz |
| 6,258,090 | B1 | 7/2001  | Jackson |
| 6,660,006 | B2 | 12/2003 | Markworth et al. |

FOREIGN PATENT DOCUMENTS

| WO | 95/14437    | 6/1995 |
| WO | 97/37604 A1 | 10/1997 |

*Primary Examiner* — Eduardo C Robert
*Assistant Examiner* — David Comstock
(74) *Attorney, Agent, or Firm* — Lerner, David, Littenberg, Krumholz & Mentlik, LLP

(57) ABSTRACT

An apparatus for securing a spinal rod within an anchoring device, wherein the anchoring device has an open end and a locking cap for securing the spinal rod within the open end. The apparatus includes a handle, an elongated body connected to the handle, a pair of jaws attached to the elongated body, a rod persuader for advancing the rod toward the anchoring device, and a locking shaft for use in locking the locking cap against the anchoring device to secure the spinal rod relative to the anchoring device.

5 Claims, 16 Drawing Sheets

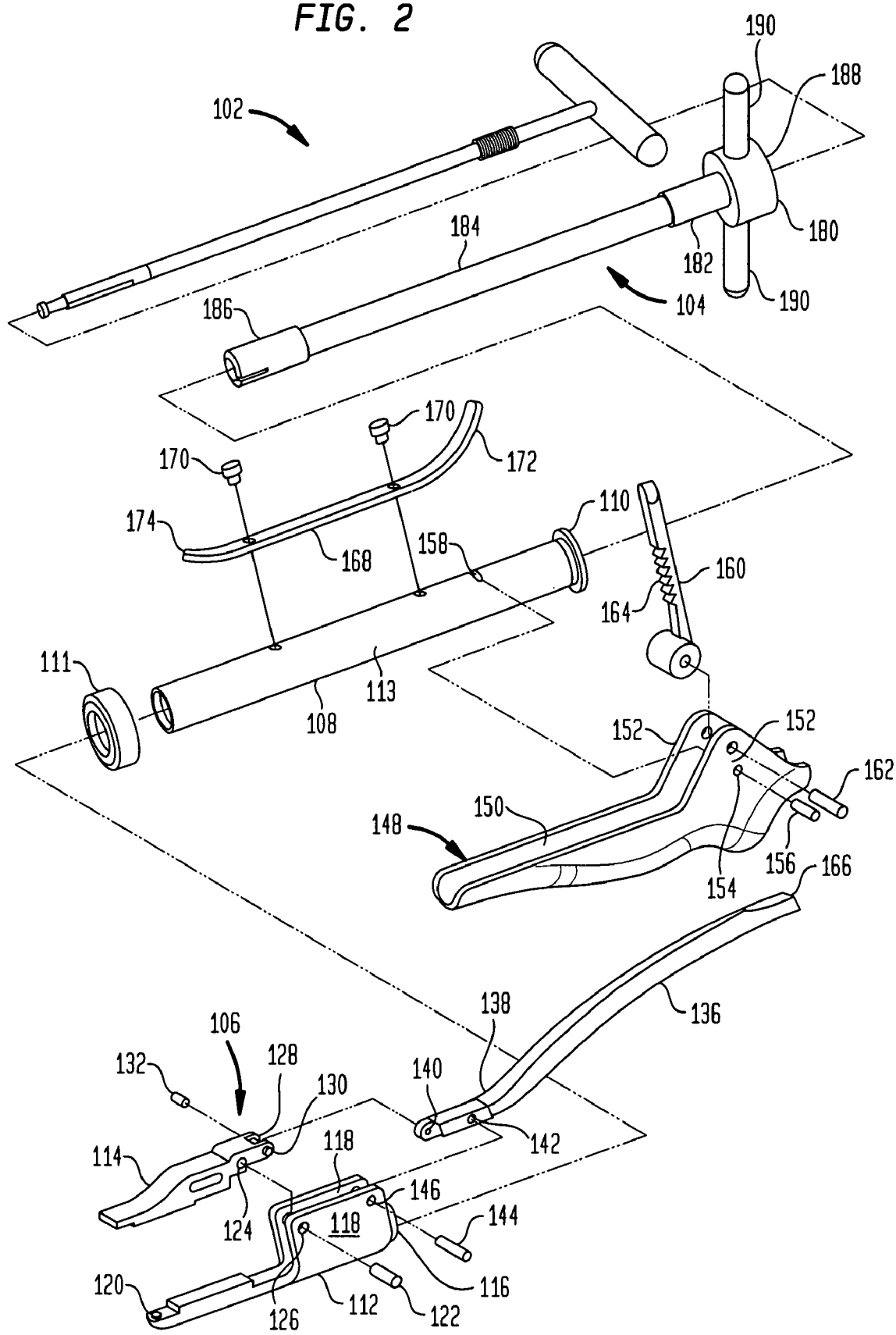

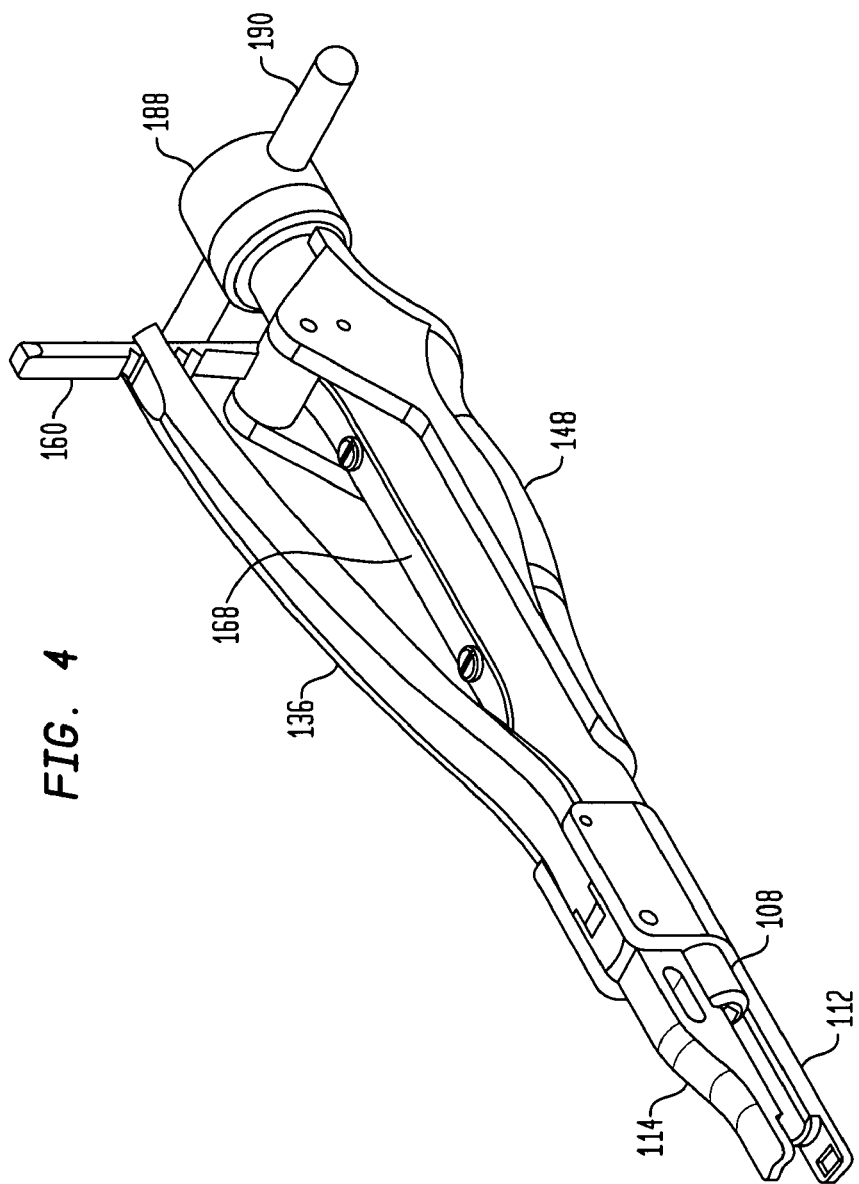
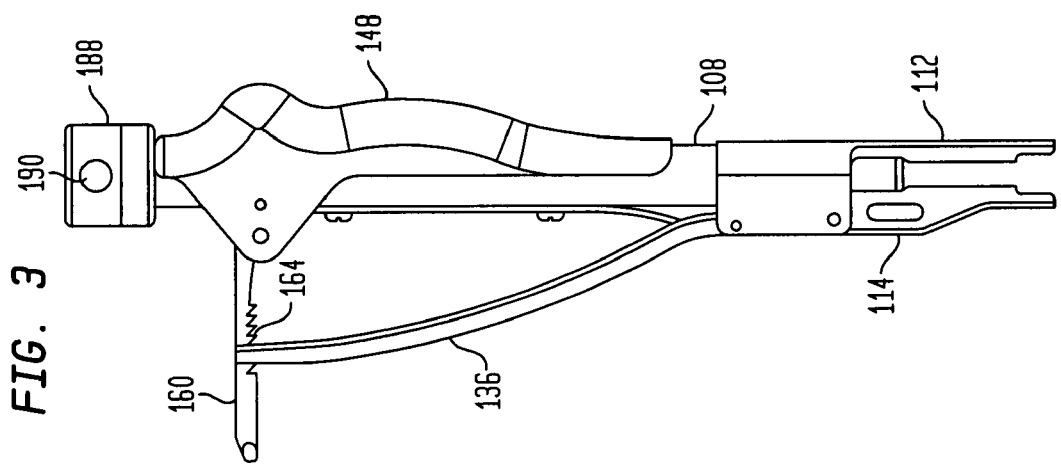

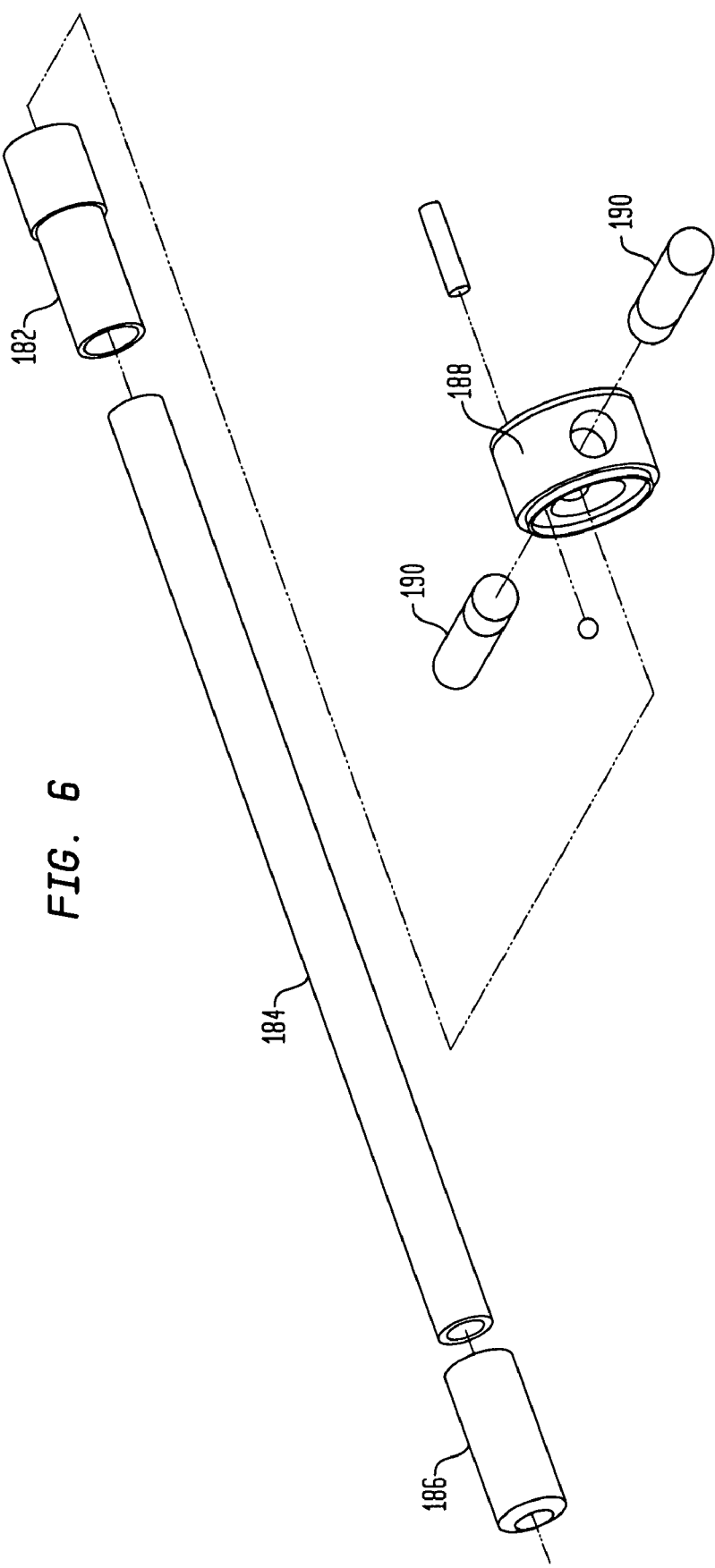

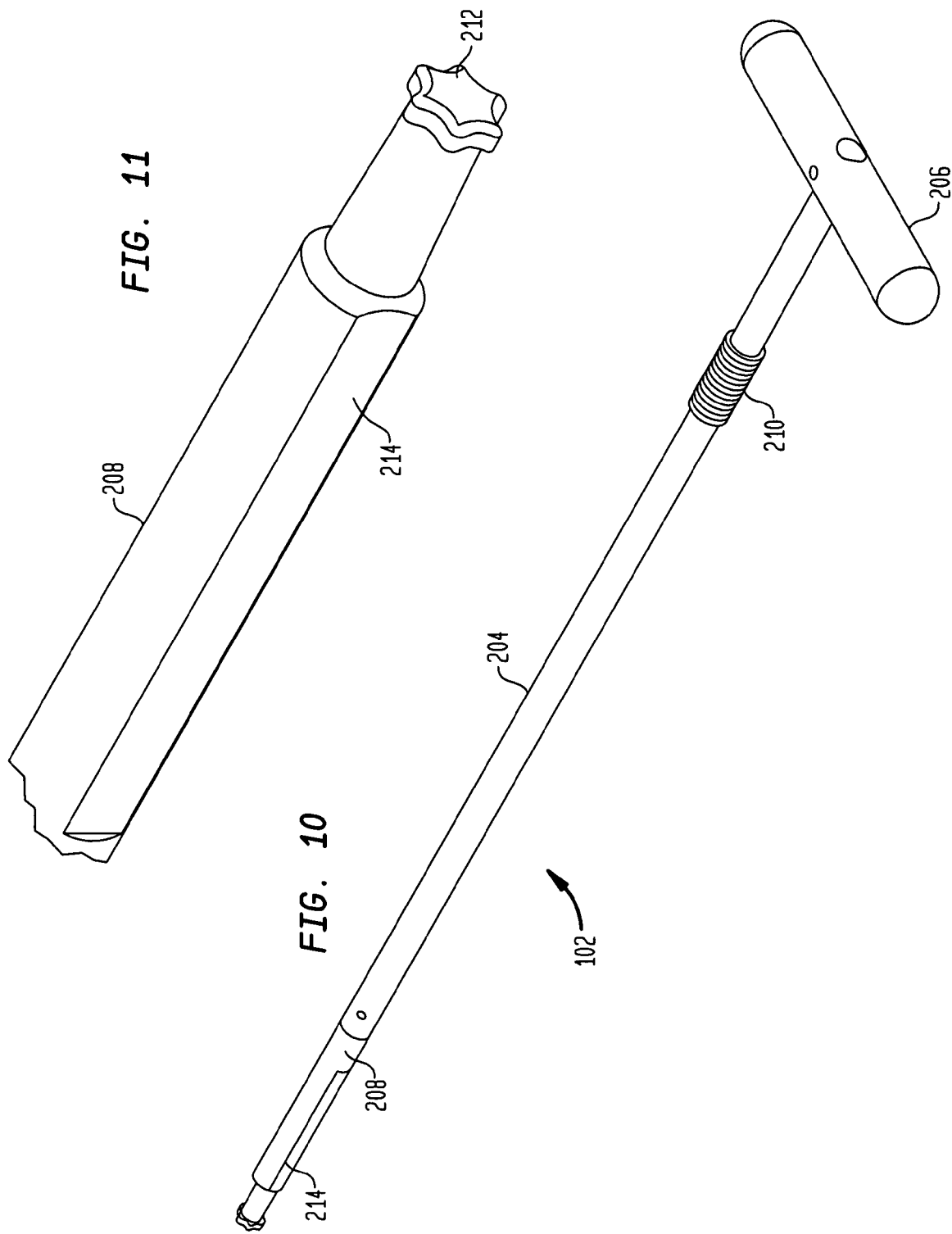

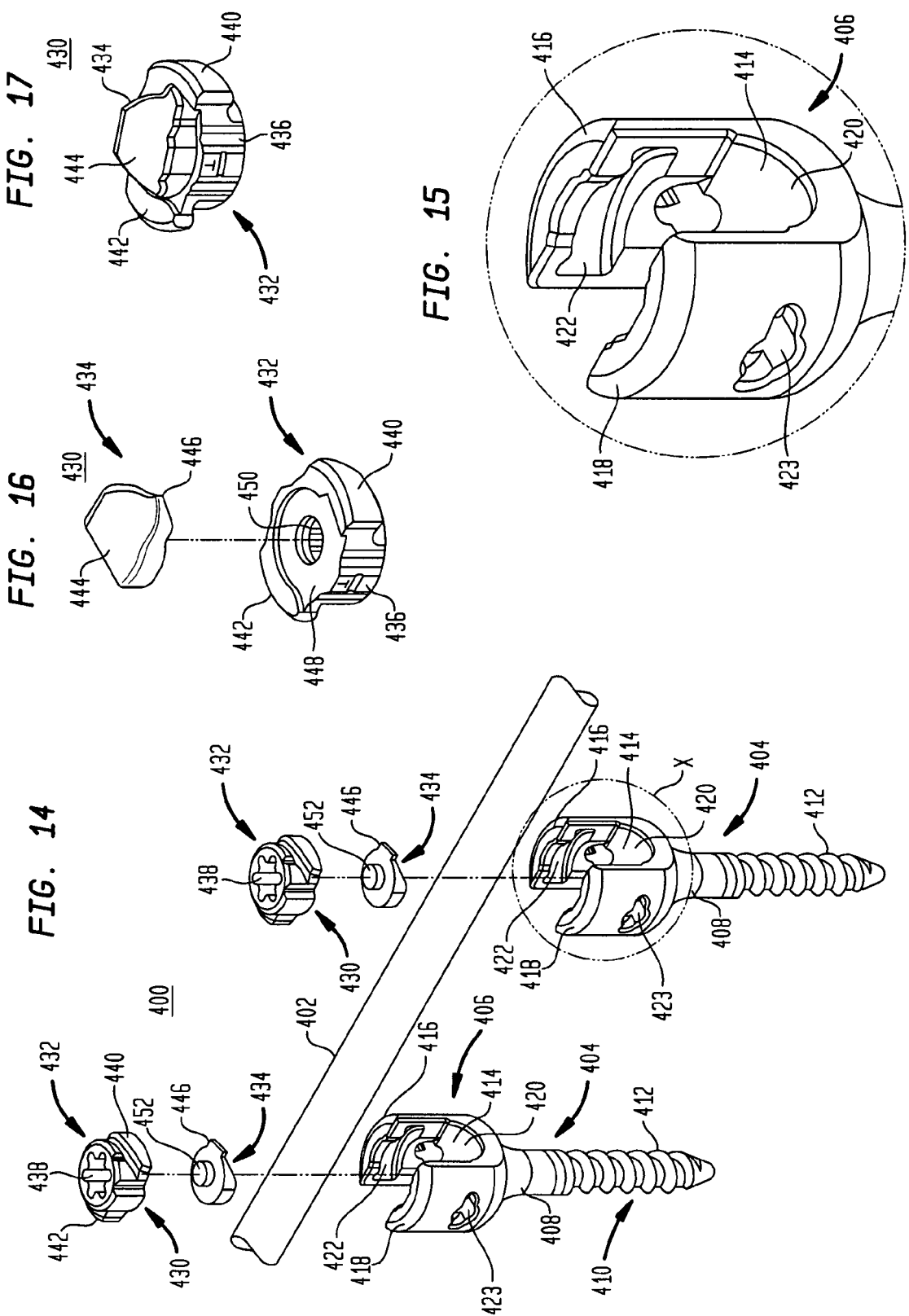

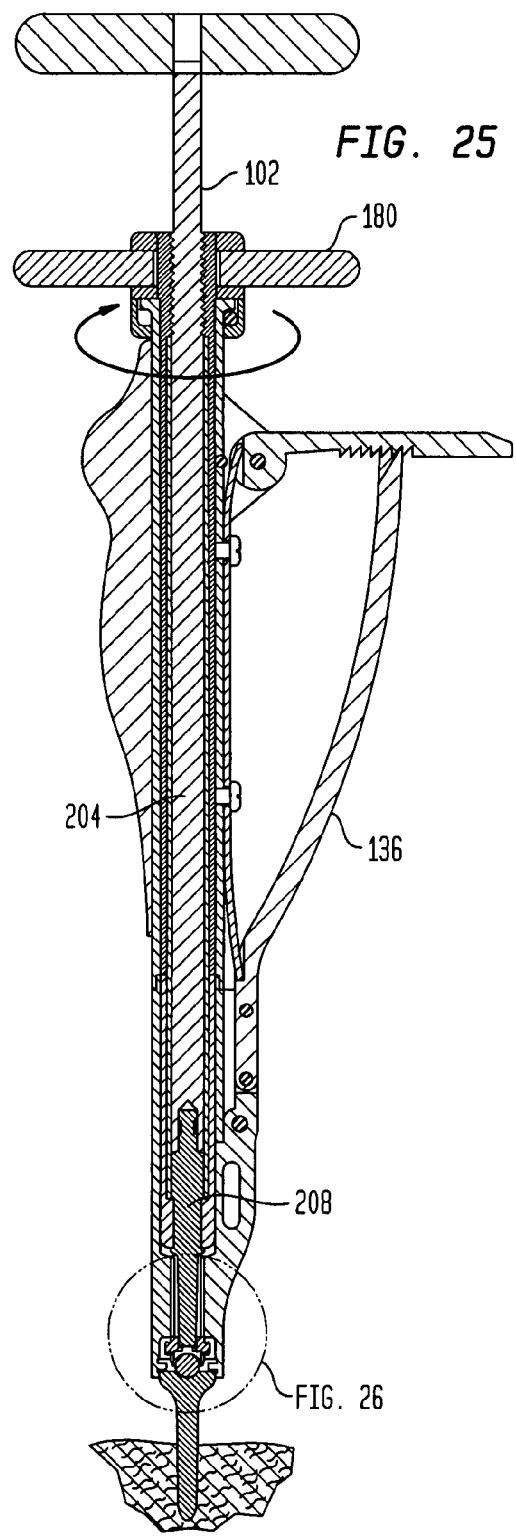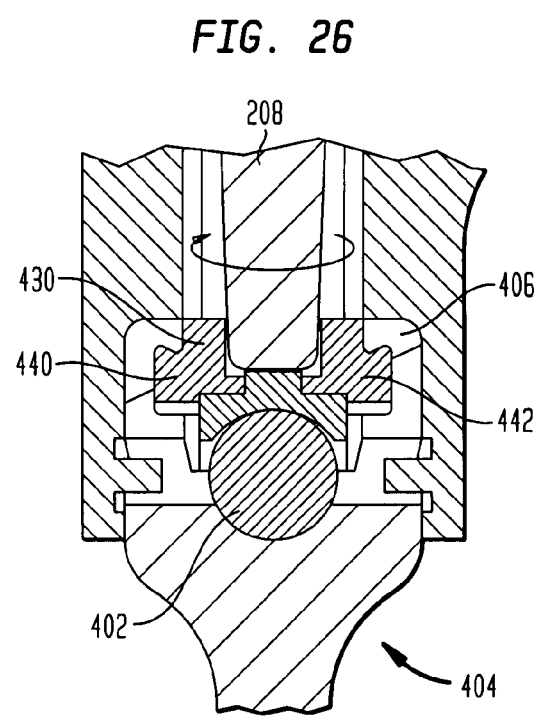

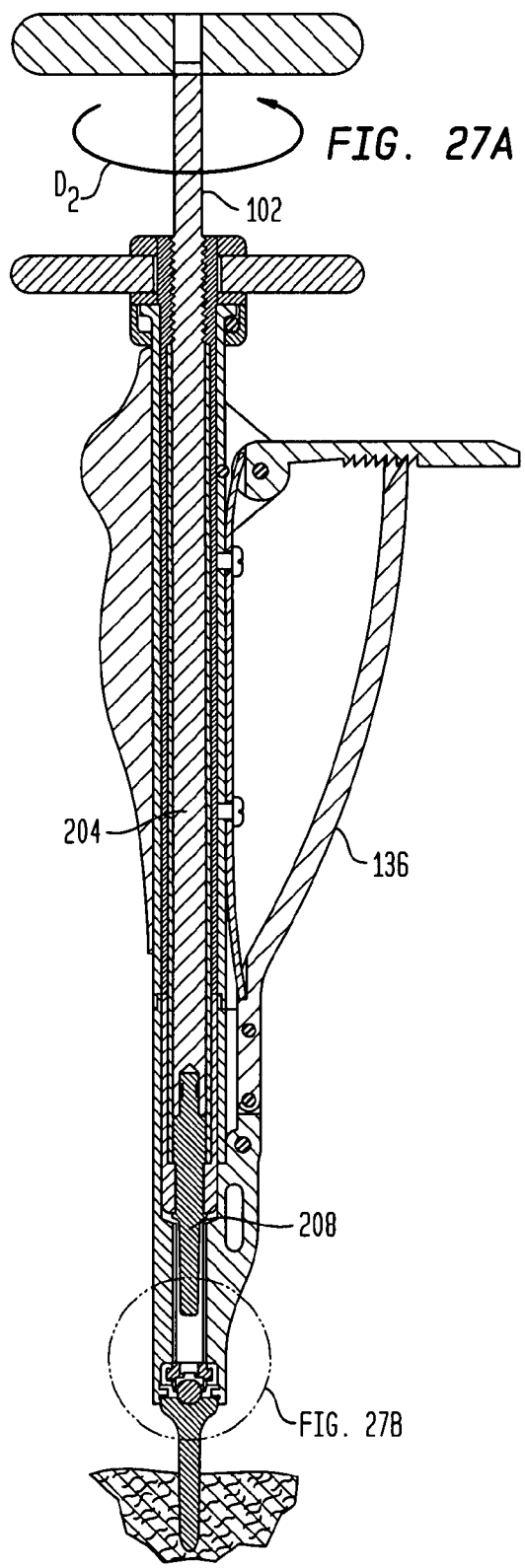
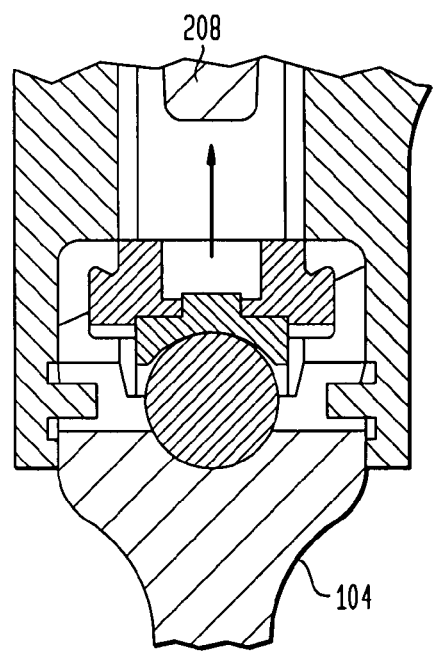
FIG. 27A
FIG. 27B

APPARATUS FOR SECURING A SPINAL ROD SYSTEM

CROSS-REFERENCE TO RELATED APPLICATIONS

This application is a divisional of U.S. application Ser. No. 10/441,764, filed on May 20, 2003, now U.S. Pat. No. 7,278, 995, which is based on U.S. Provisional Application No. 60/385,994 filed on Jun. 4, 2002, the teachings of which are incorporated herein by reference.

BACKGROUND OF THE INVENTION

The present invention relates to a surgical instrument and, more particularly, to an apparatus and method for securing a spinal rod system.

The spinal column is a complex system of bones and connective tissue which protects critical elements of the nervous system. Despite these complexities, the spine is a highly flexible structure, capable of a high degree of curvature and twist through a wide range of motion.

For many years, orthopedic surgeons have attempted to correct spinal irregularities and restore stability to traumatized areas of the spine through immobilization. Over the past ten years, spinal implant systems have been developed to achieve immobilization. Such systems often include spinal instrumentation having connective structures such as elongated rods which are placed on opposite sides of the portion of the spinal column intended to be immobilized. Screws and hooks are commonly utilized to facilitate segmental attachment of such connective structures to the posterior surfaces of the spinal laminae, through the pedicles, and into the vertebral bodies. These components provide the necessary stability both in tension and compression to achieve immobilization.

Accordingly, the subject disclosure is directed to an apparatus to facilitate securement of the screws and hooks to the connective structures of a spinal stabilization system. Specifically, the apparatus is used in connection with a spinal rod system and assists in positioning the rods of the system relative to the spinal screws and securing the system at a desired orientation.

SUMMARY OF THE INVENTION

An apparatus for facilitating securing of a spinal rod within an anchoring device having an open end and a locking cap for securing the spinal rod within the open end, includes:

a handle an elongated body connected to the handle and defining a longitudinal axis;

a pair of jaws mountable to the elongated body, the jaws adapted for relative movement between an open displaced position and a closed position, the jaws defining structure for engaging the anchoring device when in the closed position thereof;

a rod persuader at least partially disposed within the elongated body and adapted for longitudinal movement therein, the rod persuader advanceable within the elongated body to operatively engage the spinal rod to approximate the spinal rod with respect to the open end of the anchoring device; and a locking shaft disposed within the elongated body and operatively engageable with the locking cap of the anchoring device, the locking shaft movable relative to the elongated body to move the locking cap to a secured position thereof within the anchoring device to secure the spinal rod relative to the anchoring device.

The rod persuader includes mounting structure for releasably mounting the locking cap such that the locking cap engages the spinal rod upon advancing movement of the rod persuader. The locking shaft may be operatively engageable with the rod persuader upon movement of the rod persuader to an advanced position thereof wherein movement of the locking shaft causes corresponding movement of the locking cap releasably engaged to the rod persuader. The locking shaft may be adapted for rotational movement to move the locking cap of the anchoring device to the secured position thereof.

The jaws each include detents for releasably engaging corresponding structure of the anchoring device. The jaws may be spring-biased to the open position thereof. One of the jaws is preferably a stationary jaw in fixed relation to the elongated body and the other of the jaws is a movable jaw. A manually engageable lever is connected to the movable jaw. The lever may be movable to cause corresponding movement of the movable jaw between the open and closed position of the jaws. A lockout mechanism including a lockout arm engageable with the manually engageable lever may selectively secure the movable jaw in the closed position.

The locking shaft is adapted for rotational movement to move the locking cap to the secured position thereof. The locking shaft is adapted to operatively engage the locking cap upon advancing movement of the rod persuader a predetermined distance thereof whereby rotational movement of the locking shaft causes corresponding rotational movement of the locking cap. The locking shaft define a central lumen therethrough for reception of the rod persuader and the rod persuader is adapted for longitudinal movement within the locking shaft.

The locking shaft includes a keyed recess dimensioned to receive corresponding keyed structured of the rod persuader whereby rotational movement of the locking shaft causes corresponding rotational movement of the locking cap. The rod persuader may include a proximal rod portion and a distal rod portion. The proximal rod portion is adapted to rotate relative to the distal rod portion adapted for relative rotational movement. With this arrangement, the distal rod portion includes the keyed structure.

Alternatively, the rod persuader may be operatively engageable with the locking shaft such that upon movement of the rod persuader to the predetermined position thereof rotational movement of the rod persuader causes corresponding rotational movement of the locking shaft and locking cap to the secured position thereof.

BRIEF DESCRIPTION OF THE DRAWINGS

The accompanying drawings, which are incorporated in and constitute a part of the specification, illustrate embodiments of the present invention and, together with the general description given above, and the detailed description of the embodiments given below, serve to explain the principles of the present invention.

FIG. 2 is an exploded view of the apparatus with parts separated;

FIG. 3 is a side elevational view of the apparatus of FIG. 2;

FIG. 4 is a rear perspective view of the apparatus of FIG. 1;

FIG. 6 is an exploded view of the locking shaft of the apparatus;

FIG. 10 is a perspective view of the rod persuader of the apparatus;

FIG. 11 is a perspective view of a cap spin of the rod persuader;

FIG. 14 is an exploded view of a pedicle screw;

FIG. 15 is an enlarged perspective view of area "X" of FIG. 14, illustrating the head of the pedicle screw;

FIG. 16 is an exploded view of a cap of the pedicle screw as seen from below;

FIG. 17 is a perspective view of the assembled cap of the pedicle screw as seen from below;

FIG. 25 is a side cross-sectional view of the apparatus illustrating the locking of the cap of the pedicle screw to the head of the pedicle screw;

FIG. 26 is an enlarged view of area "26" of FIG. 25;

FIGS. 27A-27B illustrate release of the rod persuader from the locking cap of the pedicle screw;

DETAILED DESCRIPTION

Figures 1, 1A:
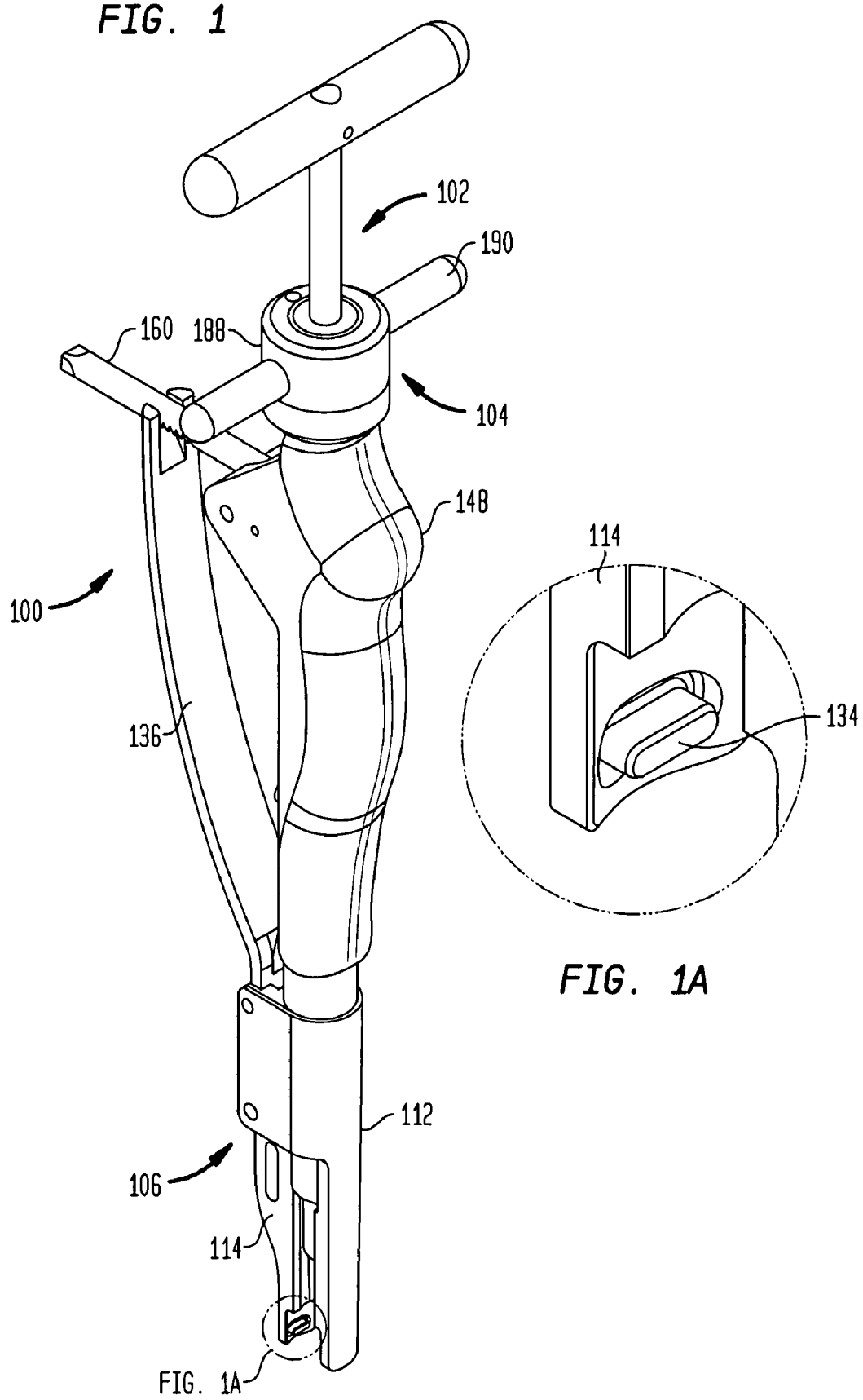
FIG. 1 is a front perspective view of the apparatus for securing a spinal rod system in accordance with the present invention.
FIG. 1A is an enlarged view of the area 1A-1A of FIG. 1.

Preferred embodiments of the apparatus for securing a spinal rod system will now be described in detail with reference to the drawing figures wherein like reference numerals identify similar or identical elements. In the drawings and in the description which follows, the term "proximal," as is traditional, will refer to the end of the apparatus closest to the operator, while the term "distal" will refer to the end of the device or instrument furthest from the operator.

Apparatus 100 is adapted for use with a spinal rod system to facilitate manipulation and securement of the rod system relative to the spine of the patient. It is envisioned that apparatus 100 may be suited for a variety of spinal rod systems which incorporate an open ended pedicle screw and a locking member positionable in the screw end for locking engagement with the rod or the screw head. Apparatus 100 is particularly adapted for use with the spinal rod system disclosed in commonly assigned application Ser. No. 09/487,942, filed Jan. 19, 2000, the contents of which are incorporated herein by reference. The spinal rod system disclosed in the '942 application will be described in further detail hereinbelow.

Referring initially to FIG. 1, the apparatus in accordance with the present disclosure, is shown generally as reference numeral 100. Apparatus 100 includes several mechanisms, namely, rod persuader 102, locking shaft 104 and jaw mechanism 106. Generally, rod persuader 102 functions in engaging a spinal rod of a spinal rod system and manipulating the rod into an open recess of the screw head. Locking shaft 104 secures the locking member of the spinal system within the open pedicle screw head. Jaw mechanism 106 mounts to the pedicle screw to stabilize the apparatus 100 relative to the spinal rod system during operation of the apparatus 100.

Figure 5:
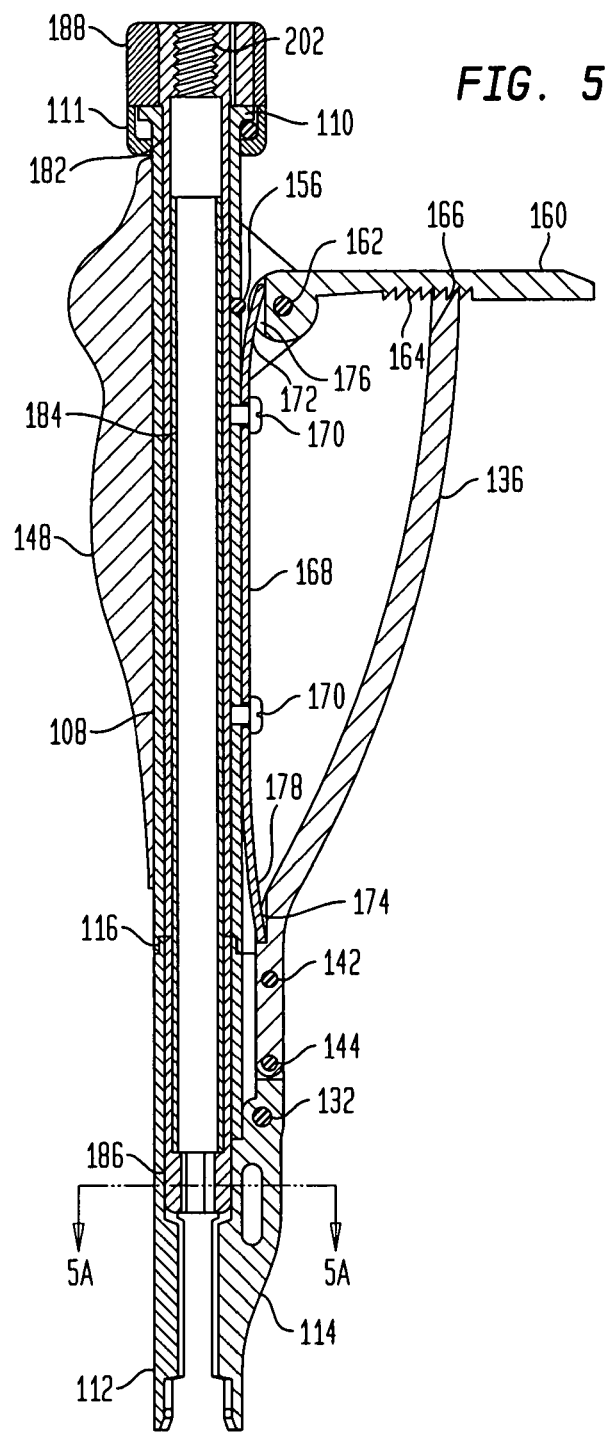
FIG. 5 is a side cross-sectional view of the apparatus with the jaw mechanism closed.

With reference to FIGS. 2-5 in conjunction with FIG. 1, jaw mechanism 106 will be initially discussed. In FIGS. 3-5, rod persuader 102 is shown removed from the apparatus 100. Jaw mechanism 106 includes tubular body 108 coaxially arranged about both rod persuader 102 and locking shaft 104. Tubular body 108 defines an enlarged flange 110 at its proximal end and collar 112 coaxially mounted about the tubular body 108 adjacent the flange 110. Tubular body 108 has fixed jaw 112 and movable jaw 114 pivotally mounted to the fixed jaw 112. Fixed jaw 112 includes proximal tubular sleeve 116 which is received within the lumen of tubular body 108 and a pair of spaced apart side walls 118 extending from the tubular sleeve 116. Fixed jaw member 112 has a region of reduced thickness and includes a tooth 120 projecting from the surface thereof. Tooth 120 defines an elongated circle or racetrack-shaped configuration having a pair of flattened opposed sides; however, it is envisioned that tooth 120 can take any shape and/or configuration.

Movable jaw 114 is pivotally mounted to fixed jaw 112 through pivot pin 122 extending through corresponding pivot holes 124, 126 of the movable jaw 114 and fixed jaw 112, respectively. Movable jaw 114 defines a clevis 128 at its proximal end. Clevis 128 has a through bore 130 for receiving connecting pin 132. Movable jaw 114 further defines tooth 134 at its distal end in diametrical opposed relation to tooth 120 of movable jaw 114. Tooth 134 is substantially identical in configuration to tooth 120 of fixed jaw 112. Tooth 134 is best depicted in FIG. 1A.

With continued reference to FIGS. 2-5, jaw mechanism 106 further includes lever 136 which is adapted for pivotal movement to cause corresponding pivotal movement of movable jaw 114. Lever 136 defines a distal region 138 which is received within side walls 118 of fixed jaw 112. Distal region 138 defines a through hole 140 which receives connection pin 132 to connect lever 136 to movable jaw 114. Distal region 138 further includes a proximal through hole 142 which receives a pivot pin 144 extending through pivot holes 146 of stationary or fixed jaw 112. Lever 136 pivots about pivot pin 144 to move movable jaw 114 between the open and closed positions.

With continued reference to FIGS. 3-5 in conjunction with FIG. 2, apparatus 100 further includes contoured handle 148. Handle 148 defines a semi-circular inner surface 150 correspondingly dimensioned to cooperate with the outer surface of tubular body 108. Handle 148 includes a pair of spaced apart walls 152 extending from circular inner surface 150. Walls 152 include a first pair of holes 154 which receive pin 156. Pin 156 is accommodated within an arcuate recess 158 formed in an outer surface 110 of the tubular body to thereby axially and rotatably fix tubular body 108 relative to handle 148.

Handle 148 further includes rack 160 pivotally connected to handle 148 through pivot pin 162. Rack 162 has a plurality of ratchet teeth 164 adapted to cooperate with proximal tooth 166 of lever 136 to selectively secure the lever 136 and thus move movable jaw 114 at desired positions between the open and closed positions thereof.

As best depicted in FIGS. 2 and 5, apparatus 100 further includes a leaf spring 168 connected to the outer surface of tubular body 108 by fasteners 170. Leaf spring 168 includes resilient proximal and distal free ends 172, 174. Proximal and distal free ends 172, 174 are adapted to engage respective recesses 176, 178 formed in rack 160 and lever 136. Accordingly, with this arrangement, leaf spring 168 functions to both bias the rack 160 into engagement with lever 136 and bias lever 136 towards a position corresponding to a closed position of movable jaw 114.

Figure 7:
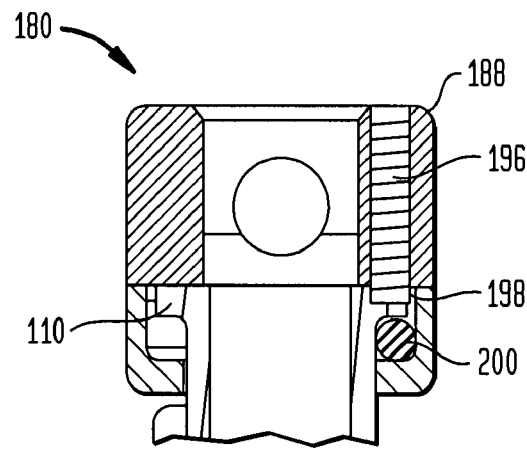
FIG. 7 is a cross-sectional view of a handle assembly of the locking shaft.
Figure 8:
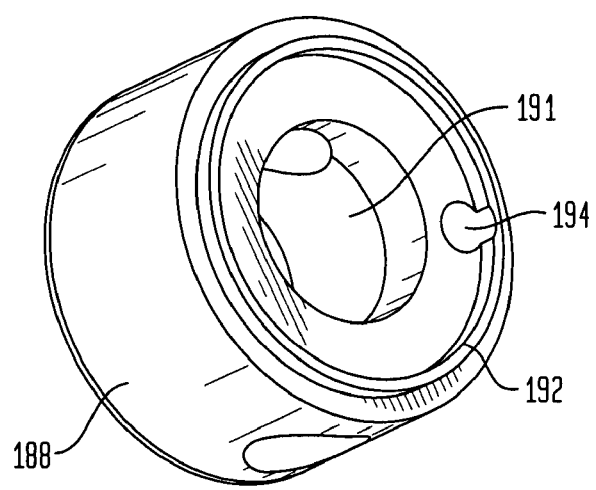
FIG. 8 is a perspective view of a handle housing of the handle assembly shown in FIG. 7.

Referring now to FIGS. 6-8, in conjunction with FIGS. 2 and 5, locking shaft 104 will now be discussed. Locking shaft 104 includes several components operatively connected to each other, namely, from proximal to distal, handle 180, connecting sleeve 182 partially disposed within the handle 180, main body 184 and socket 186 connected to the main body 184. Handle 180 has a cylindrical housing 188 and a pair of diametrically opposed handles 190 (FIG. 6) extending radially from the housing 188. Handle assembly 180 includes through bore 191 extending centrally therethrough and an annular rim 192 integrally formed in a distal surface thereof. Preferably, annular rim 192 is spaced a distance from a terminal edge of the distal surface of housing 188. Housing 188 further includes an off-axis through axial bore 194.

Figure 9:
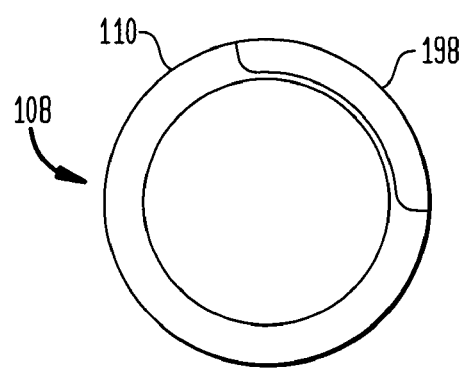
FIG. 9 is an axial view of the tubular body.

A dowel 196 is received within axial bore 194 and projects from the distal surface of housing 188 for reception within a recess 198 defined in the proximal surface or flange 110 of tubular body 108. FIG. 9 is an axial view of the configuration of recess 198 of tubular body 108. As shown, the recess 198 extends through an arc of about 45 degrees relative to the axis of the tubular body. Thus, handle 180 is capable of rotation relative to the tubular body 108 through an angle equal to the arc of recess 198 of flange 110, i.e., 45 degrees. Other angular recesses are envisioned as well. Bearing 200 is provided to facilitate rotational movement of handle 180 (FIG. 7).

Figure 5A:
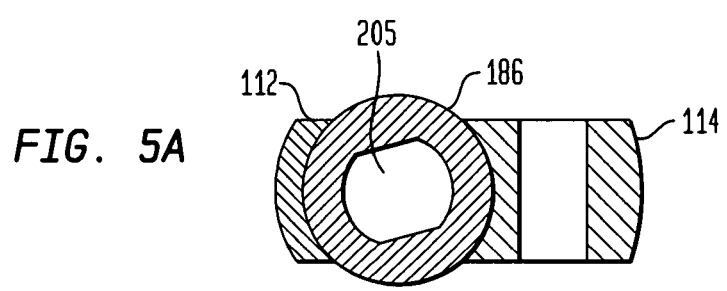
FIG. 5A is a cross-sectional view taken along the lines 5A-5A of FIG. 5.

Connecting sleeve 182 of locking shaft 104 is mounted about the proximal end of main body 184 and secured thereto via an interference fit or other conventional means. Connecting sleeve 182 is securely mounted within bore 191 of handle 180 and defines an internal thread 202 (FIG. 5). Socket 186 of locking shaft 104 is partially mounted about main body 184. Socket 186 defines an internal opening or keyed structure 205 having a racetrack configuration as depicted in the cross-sectional view of FIG. 5A.

Referring now to FIGS. 10-13, in conjunction with FIGS. 1-2, rod persuader 102 will be discussed in detail. Rod persuader 102 includes rod shaft 204 having handle 206 mounted at its proximal end and cap spin 208 coupled to its distal end. Rod shaft 204 includes a helical thread 210 adjacent its proximal end. Helical thread 210 is adapted to engage internal helical thread 202 of connecting sleeve 182 whereby rotational movement of the rod shaft 204 causes the shaft 204 to axially translate. Cap spin 208 includes a shaped tip 212 for engaging a rear end of a locking cap of the spinal rod system as will be discussed. As seen in FIG. 11, shaped tip 212 has a torx configuration, however, alternative configurations may also be utilized to facilitate axial rotation of the locking cap, such as, for example, cruciform, polygonal, hexagonal, etc. In addition, cap spin 208 includes a pair of opposed planar surfaces 214 to define a cross-section of the cap spin 208 which corresponds for reception within keyed opening 202 of socket 186 upon advancement of rod shaft 204 a predetermined distance.

Figure 12:
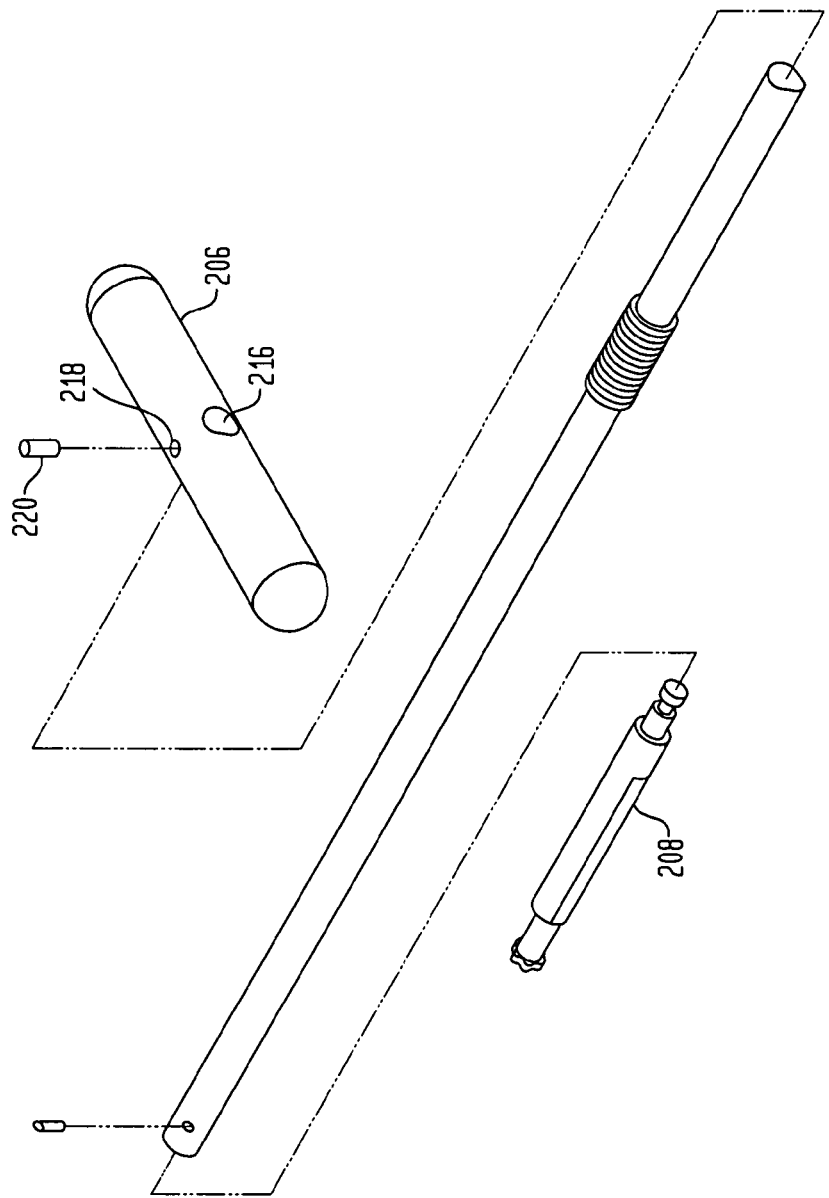
FIG. 12 is an exploded view with parts separated of the rod persuader.
Figure 13:
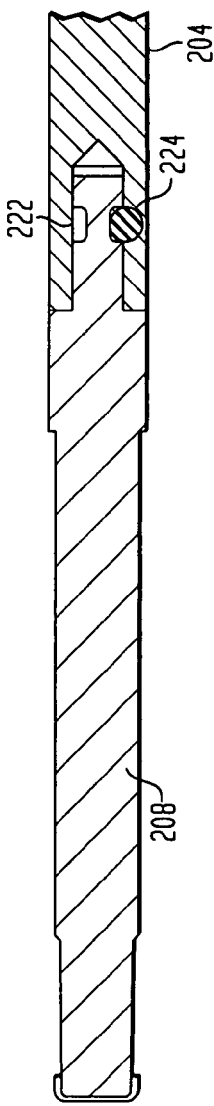
FIG. 13 is a cross-sectional view of the cap spin.

With reference to FIG. 12, handle 206 includes a through bore 216 sized and shaped to receive the proximal end of rod shaft 204 therein. Preferably, handle 206 includes a threaded opening 218 which is formed transverse to bore 216 and receives a lock screw 220 for engaging the outer surface of rod shaft 204 and thus prevents handle 206 from separating from rod shaft 204. Cap spin 208 is rotatably mounted to rod shaft 204 through a slip fit connection effected by circumferential recess 222 of the cap spin 208 and slip pin or bearing 224 extended through a bore in rod shaft 204 and received within the recess 222.

Referring now to FIGS. 14-17, the spinal rod system intended for use with instrument 100 is illustrated in detail. As discussed hereinabove, this system is disclosed in commonly assigned application Ser. No. 09/487,942. Spinal rod system 400 includes an elongated spinal rod 402 having a circular cross-section and a substantially smooth outer surface finish. As illustrated, anchoring devices in the form of bone screws 404 are provided for securing spinal rod 402 to the spine during a spinal stabilization procedure.

With continuing reference to FIGS. 14-17, and in particular to FIGS. 14 and 15, bone screw 404 includes a head portion 406 defining a horizontal and a vertical axis. A shank portion 408 depends from head portion 406 and a threaded portion 410 having a helical thread 412 extending about the outer periphery depends from shank portion 408. Helical thread 412 is particularly adapted to securely engage the vertebral bodies of the spine. Head portion 406 defines a substantially U-shaped channel 414, formed along the horizontal axis thereof, for receiving spinal rod 402. In particular, U-shaped channel 414 is defined by the interior surfaces of side walls 416 and 418 and curved lower wall 420, which extends therebetween. Head portion 406 further includes an elongated slot 423 formed in each side wall 416, 418. It is envisioned that slots 423 are configured and adapted to receive tooth 120 of fixed jaw member 122 and tooth 146 of movable jaw member 124.

Bone screw 404 includes a locking cap 430 having an upper portion 432 and a lower portion 434. Upper portion 432 includes a substantially cylindrical cap body 436 defining an axial reception port 438 for receiving and cooperating with shaped tip 212 of cap spin 208 of rod persuader 102. Upper portion 432 further includes a pair of circumferentially opposed arcuate engagement flanges 440, 442 which extend radially outward from cap body 436. Engagement flanges 440, 442 include oppositely inclined, radially inward sloping, camming surfaces for cooperating with a corresponding complimentary inner opposed arcuate engagement slot 422, 424 formed in opposed side walls 416, 418 of head portion 406. Flanges 440, 442 of locking cap 430 become engaged in corresponding slots 422, 424 upon rotation of upper portion 432 of locking cap 430 relative to head portion 406 of bone screw 404.

Lower portion 434 of locking cap 430 is configured and adapted for cooperative reception within U-shaped channel 414 of head portion 406 and is adapted to engage spinal rod 402 extending through U-shaped channel 414. More particularly, lower portion 434 has a curved exterior surface which compliments the interior curvature of side walls 416, 418 of had portion 406. Lower portion 434 of locking cap 430 is provided with a hemi-cylindrical channel 444 formed in an undersurface thereof for engaging and cooperating with spinal rod 402 upon loading of locking cap 430 in U-shaped channel 414. Lower portion 434 includes a radially extending flange 446 which aides in the alignment and positioning of lower portion 434 with respect to spinal rod 402.

As been seen in FIG. 16, the lower surface of upper portion 432 of locking cap 430 includes a recessed seating area 448 and an associated axial reception bore 450. Recessed seating area 448 is configured and dimensioned to accommodate lower portion 434, while reception bore 450 is configured and dimensioned to receive and engage an axial post 452 which projects from an upper surface 454 of lower portion 434 of locking cap 430. The interaction of axial post 454 and axial reception bore 450 facilitates relative rotational movement of upper portion 432 relative to lower portion 434 when locking cap 430 is loaded into and locked in head portion 406 of bone screw 404 during a spinal stabilization procedure.

Use of a two-part locking cap enables a surgeon to load locking cap 430 into U-shaped channel 414 and properly position lower portion 434 against spinal rod 402 so as to ensure a tight engagement between hemi-cylindrical channel 444 and the cylindrical surface of the spinal rod. Thereafter, upper portion 432 may be rotated into a locked position relative to lower portion 434.

During a spinal stabilization procedure, bone screws 404 are first implanted into the vertebral bodies of the spine and spinal rods 402 are then fitted into U-shaped channels 414 of each bone screw 404. Once bone screws 404 are in place and spinal rod 402 seated within U-shaped channels 414, locking caps 430 are loaded into head portion 406. At such a time, hemi-cylindrical channel 444 of lower portion 434 will engage the cylindrical surface of spinal rod 402 and be maintained in a fixed axial orientation with respect to spinal rod 402 due to the mating relationship between lower portion 434 and U-shaped channel 444.

Locking cap 430 is preferably loaded in such a manner so that the radially outward extending engagement flanges 440, 442 of upper portion 432 are parallel to the axis of spinal rod 402. Once upper portion 432 of locking cap 430 has been properly oriented with respect to head portion 406, with radially extending flange 446 aligned with spinal rod 402, upper portion 432 is rotated in a clockwise direction relative to lower portion 434 of locking cap 430 using an appropriate rotational tool, e.g., apparatus 100. Thereupon, arcuate engagement flanges 440, 442 of upper portion 432 engage corresponding engagement slots 422, 424 to drive the locking cap 430 into engagement with the spinal rod 402. Once rotated into a locked position, lower portion 434 of locking cap 430 is seated within recesses seating area 448 defined in the bottom surface of upper portion 432 of locking cap 430. At such a time, the position of head portion 406 of bone screw 404 is fixed with respect to the longitudinal axis of spinal rod 402. As appreciated, locking cap 430 rotates through approximately 45 degree arc to assume the secured position thereof.

Figure 18:
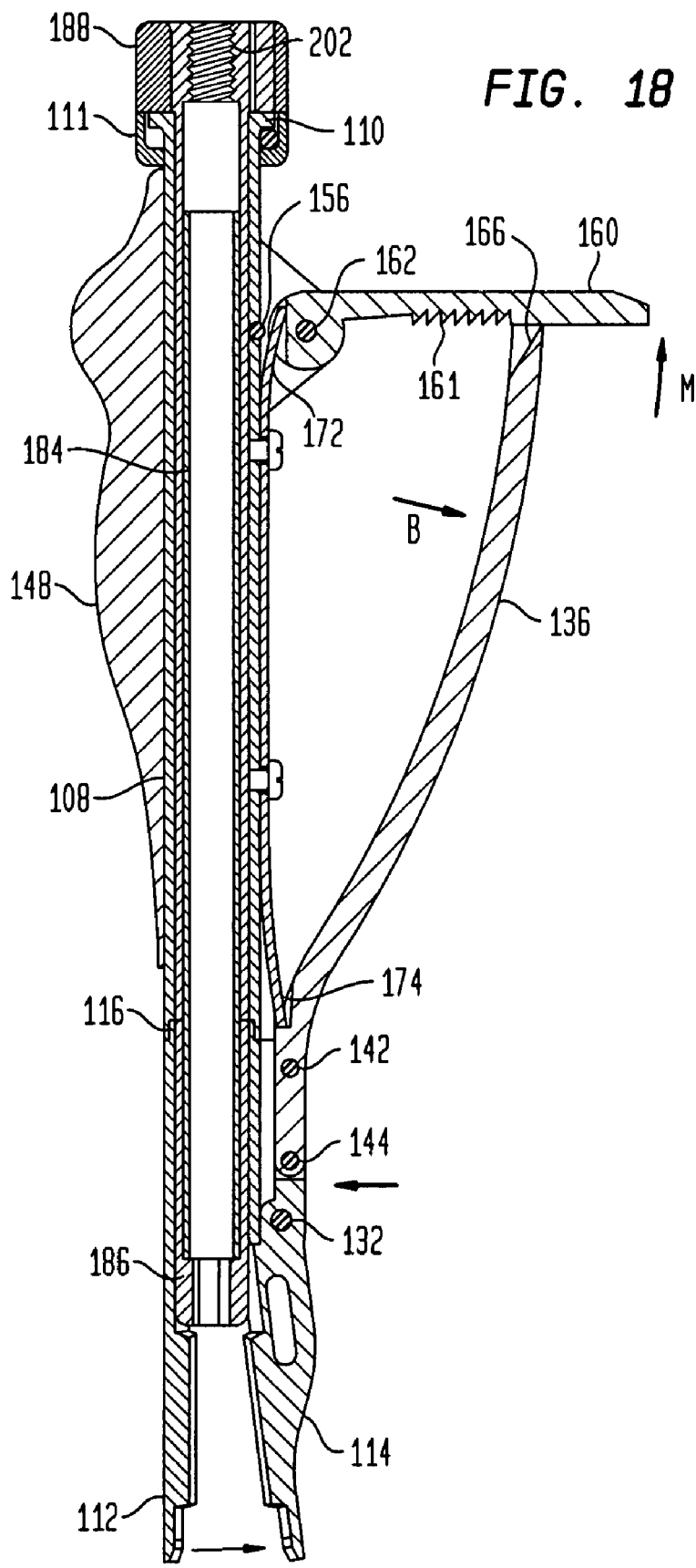
FIG. 18 is a cross-sectional view of the apparatus with the jaw mechanism in the open position.

Turning now to FIG. 18, use of a rod apparatus 100 in conjunction with spinal stabilization system 400 will be shown and described. Initially, with reference to FIG. 18, jaw mechanism 106 of apparatus 100 is moved from the closed position of FIG. 5 to the opened position of FIG. 18. In order to open jaw assembly 106, the surgeon manipulates rack 160 in a direction "A1," to overcome the spring bias of proximal free end 172 of leaf spring 168 acting on planar surface of rack 160 to thereby disengage tooth 166 of lever 136 from teeth 164 of rack 160. With proximal end 172 of lever 168 disengaged, lever 136 is automatically pivoted about pivot pin 144 by a spring force acting in a direction "B" on recess 208 by distal free end 174 of leaf spring 168, thereby moving lever 136 away from tubular body 108 and causing movable jaw 114 to pivot to the open position depicted in FIG. 18. It is appreciated that lever 136 does not need to be spring biased to perform the operation.

Figure 19A:
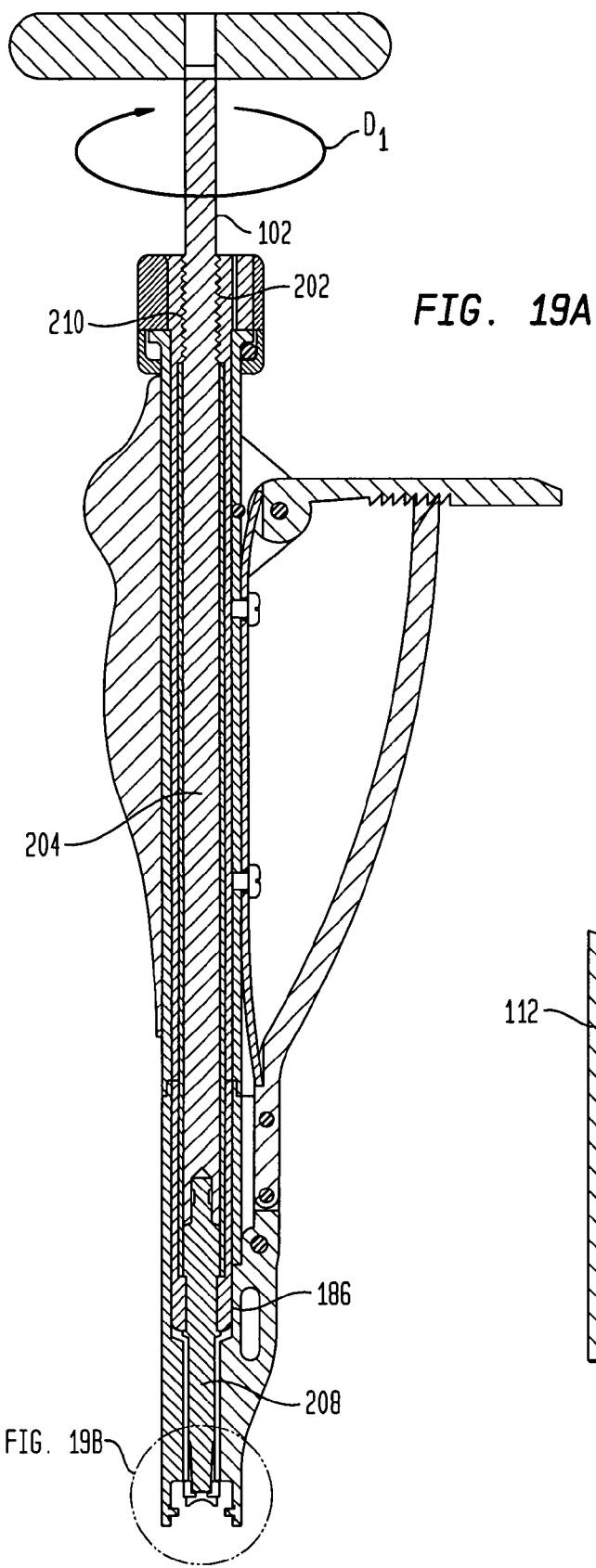
FIGS. 19A-19B are cross-sectional views of the apparatus with the rod persuader advanced for mounting the locking cap of the spinal rod system.
Figure 19B:
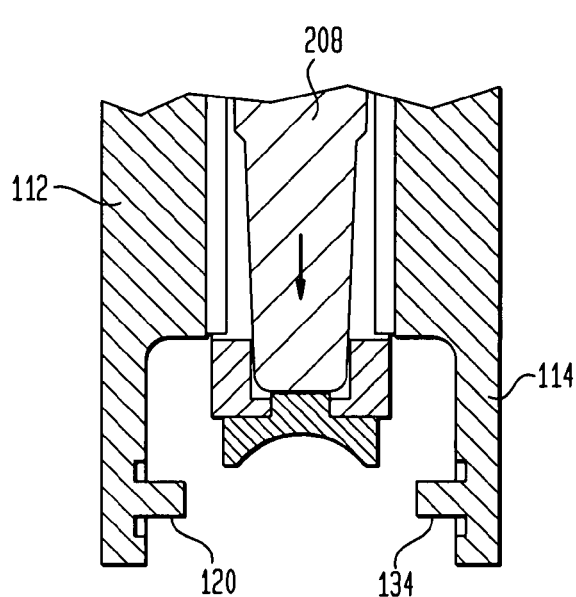

Referring now to FIGS. 19A and 19B, attention is directed to mounting locking cap 430 of spinal rod system 400 onto rod persuader 102. Rod persuader 102 is introduced within locking shaft 104 and tubular body 108, and advanced via rotation (in the direction D1) until cap spin 208 projects distally beyond socket head 186 of locking shaft 106 and within jaw mechanism 106. Locking cap 430 is loaded onto shaped tip 212 of cap spin 208 with reception port 438 receiving the tip 212 in frictional relation therewith. Once locking cap 430 is mounted, rod persuader 102 is retracted by rotating handle 206 in a counterclockwise direction to withdraw locking cap 430. It is noted that in the withdrawn position of locking cap 430, cap body 436 is received within the arcuate recesses of the jaw mechanism while flanges 440, 442 of the locking cap 430 extend through the linear spaces defined between fixed and movable jaws 112, 114. Thus, locking cap 430 is in a fixed angular position within jaw mechanism 106. It is also appreciated that apparatus 100 may be pre-loaded with a locking cap 430 thereby obviating the aforementioned loading step.

Figure 20:
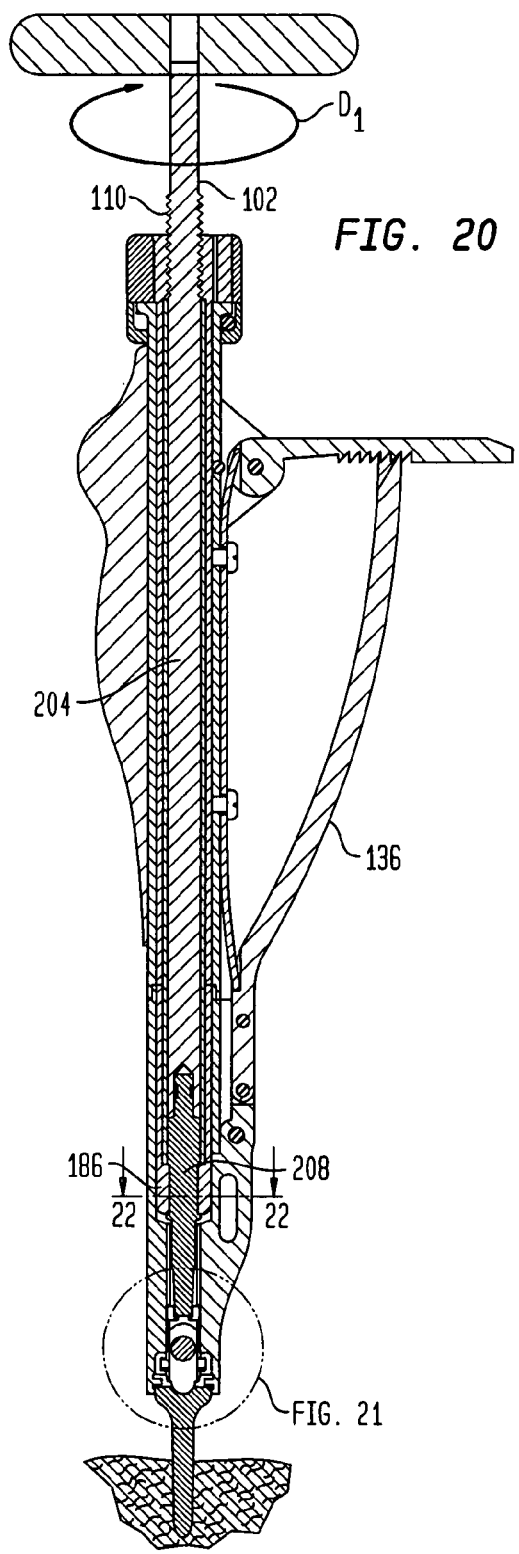
FIG. 20 is a side cross-sectional view of the apparatus of FIG. 1, shown mounted on to the head of the pedicle screw.
Figure 21:
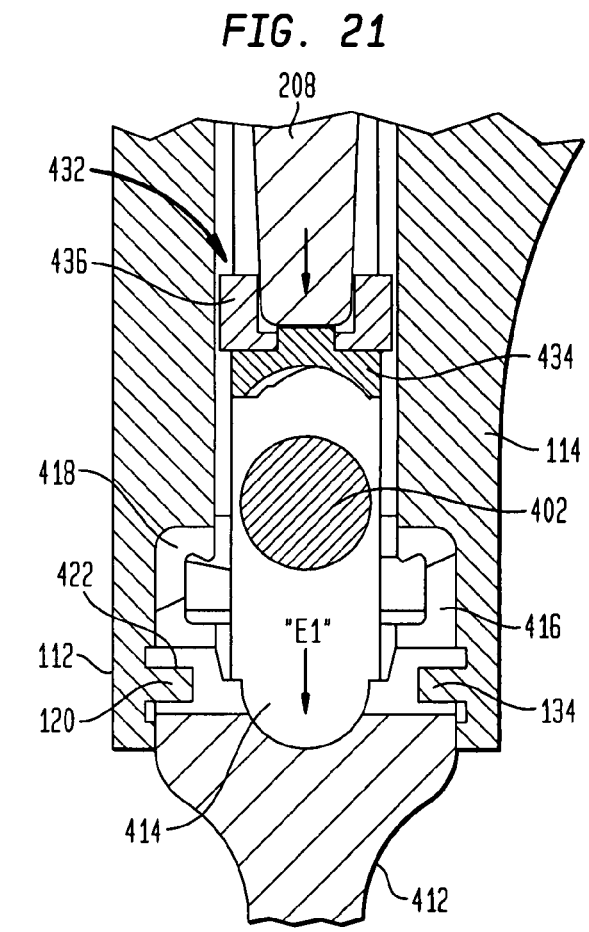
FIG. 21 is an enlarged view of area "21" of FIG. 21.
Figure 22:
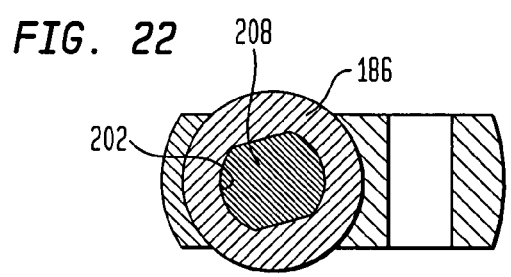
FIG. 22 is a cross-sectional view of the apparatus taken at "22-22" of FIG. 20.

With bone screw 404 secured into a vertebrae "V" and spinal rod 402 positioned generally adjacent U-shaped channel 414 of bone screw 404, jaw mechanism 106 is coupled to head portion 406 of bone screw 404. In particular, lever 136 is moved toward handle 148 to cause pivotal movement of movable jaw 114 to the closed position depicted in FIGS. 20 and 21. In the closed position, teeth 120, 134 of fixed and movable jaws 112, 114 are received within correspondingly dimensioned slots 423 of screw head portion 406. Jaw assembly 106 is locked onto head portion 406 by the ratcheting engagement of teeth 164 of rack 160 with tooth of lever 136.

Rod persuader 102 is then rotated in a direction "D1," wherein helical threads 210 of rod shaft 204 engage internal threads 196 of connecting sleeve 182 to thereby distally displace rod shaft 204. During distal movement of rod shaft 204, locking cap 430 mounted to cap spin 286 of rod shaft 204 engages spinal shaft 402 to drive spinal shaft 402 in direction "E1," i.e., into U-shaped channel 414 of bone screw 404. It is appreciated that during rotation of rod shaft 204 cap spin 208 does not rotate due to the slip fit connection depicted in FIG. 13 and discussed hereinabove and the engagement of cap body 436 within the interior surfaces of jaws 112, 114.

Figure 23:
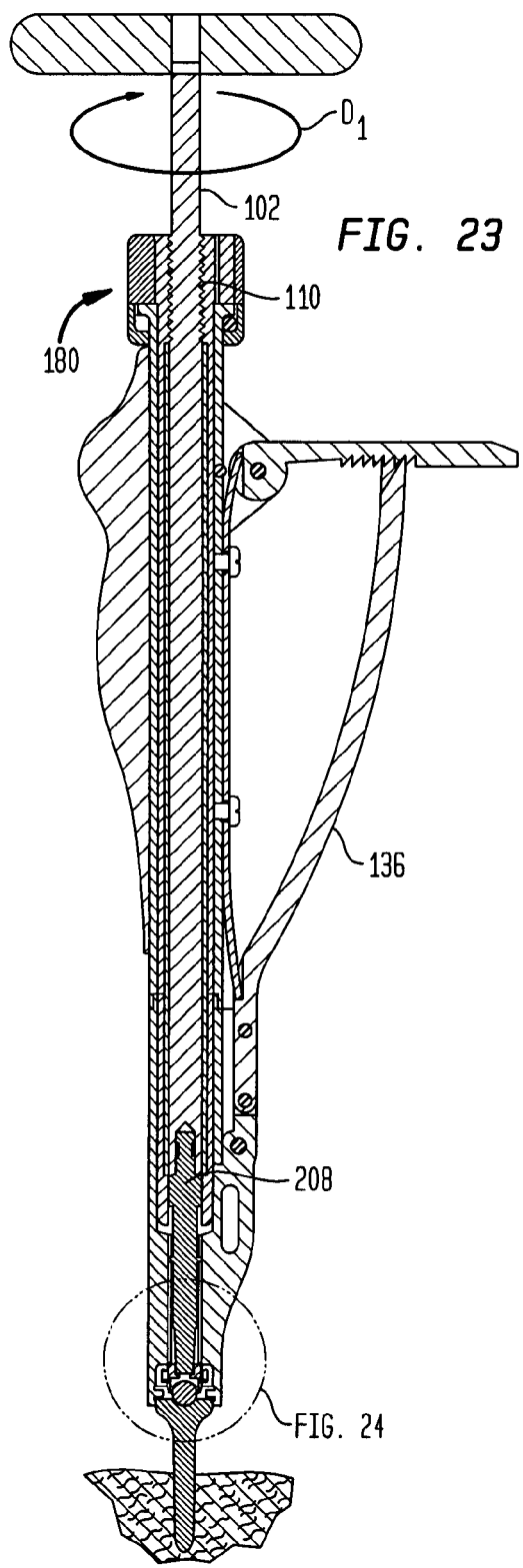
FIG. 23 is a side cross-sectional view of the apparatus illustrating the positioning of a rod in the head of the pedicle screw.
Figure 24:
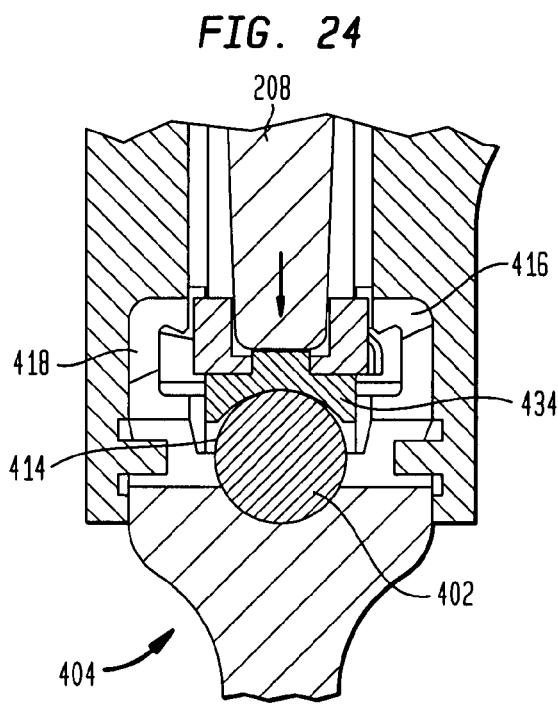
FIG. 24 is an enlarged view of area "24" of FIG. 23.

Rod shaft 204 is rotated in direction "D1" until spinal shaft 402 and locking cap 430 are fully seated within U-shaped channel 414 of bone screw 404, as seen in FIGS. 23 and 24. Thereafter, handle assembly 180 of locking shaft 104 is rotated through a 45 degree arc of rotation (relative to tubular body 108 discussed hereinabove) to cause corresponding rotation of main body 184 and socket 186 of the locking sleeve 104. As socket 186 rotates, the keyed structure f socket head 186 and cap spin 208 causes the cap spin 208 and thus locking cap 430 to rotate. As seen in FIGS. 25 and 26, the rotation of locking cap 430 also results in engagement flanges 440, 442 being rotated into respective camming slots 422, 424 of head portion 406 of bone screw 404 thereby locking spinal rod 402 in U-shaped channel 414 of bone screw 404 in compressive relation therewith.

Figure 27C:
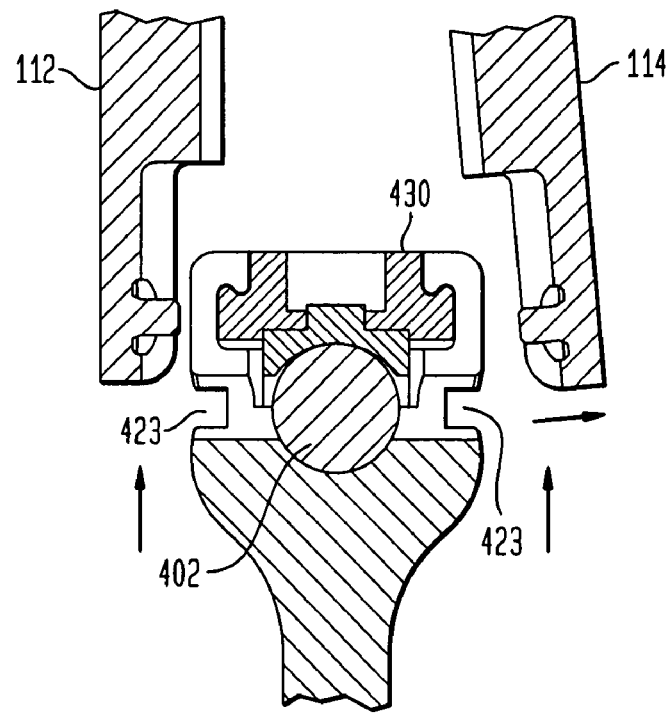
FIG. 27C is an enlarged view illustrating the opening of the jaw mechanism.

With reference to FIGS. 27A-27C, following the fixation of locking cap 430 and spinal rod 402 to bone screw 404, rod shaft 204 is rotated in a direction "D2," opposite direction "D1," to withdraw rod persuader 102 and to disengage shaped tip 212 of cap spin 208 from locking cap 430. Jaw assembly 120 is then opened as depicted in FIG. 27C to remove the apparatus.

Figure 28:
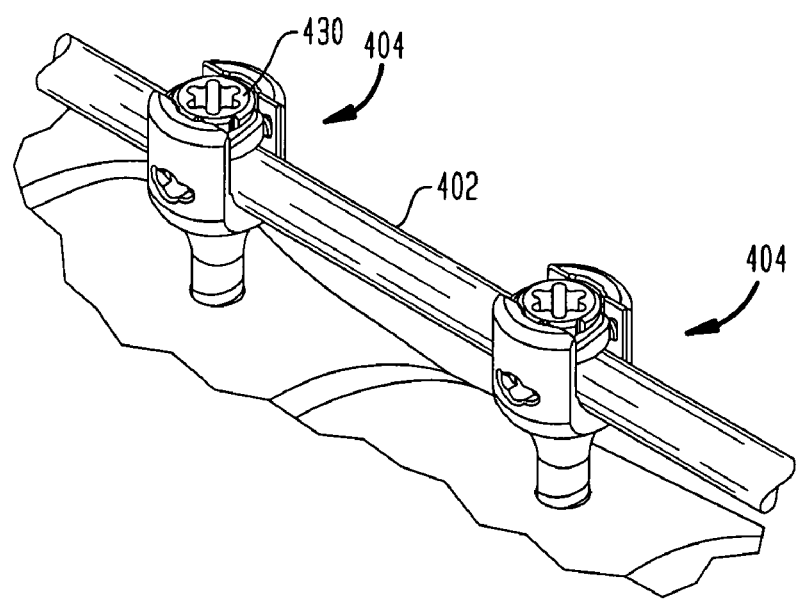
FIG. 28 is a perspective view of a pair of pedicle screws secured to a vertebral body and having a rod extending through the pair of pedicle screws.

As seen in FIG. 28, rod persuader 100 can be used multiple times to lock a spinal rod 402 to multiple bone screws 404 which are screwed into vertebrae "V" of the spinal chord.

While the invention has been illustrated and described in detail in the drawings and foregoing description, the same is to be considered as illustrative and not restrictive in character, it being understood that only the preferred embodiments have been shown and described to be protected. For example, it is envisioned that continued rotation of rod persuader 102 may effectuate locking of the locking cap within the screw 404 without requiring separate rotation of the handle 180 of the locking shaft 104 by the user. In this regard, the rod persuader may be mechanically connected (through a friction fit, etc. . . . ) to the locking shaft such that rotation of the rod persuader subsequent to driving the spinal rod within the screw head will cause rotation of the locking shaft and thus the locking cap. It is envisioned with this arrangement that handle 180 of the locking shaft may be engaged to secure the locking shaft during rotating withdrawal of the rod persuader 102 from the apparatus 100.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of securing a spinal rod to an anchoring device using a surgical instrument having a proximal end and a distal end, the method comprising:
   releasably attaching a locking cap to the distal end of the surgical instrument,
   positioning the surgical instrument to facilitate operative engagement with the spinal rod,
   engaging the anchoring device between a stationary jaw and a movable jaw of the distal end of the surgical instrument,
   urging the spinal rod toward the anchoring device by advancing the locking cap, and
   securing the spinal rod to the anchoring device by using the surgical instrument to attach the locking cap to the anchoring device while capturing the spinal rod between the locking cap and the anchoring device.

2. The method of claim 1, wherein releasably attaching the locking cap to the distal end of the surgical instrument involves frictionally fitting the locking cap onto a shaped tip portion of the distal end of the surgical instrument.

3. The method of claim 1, wherein engaging the anchoring device with the distal end of the surgical instrument involves clamping the anchoring device with a jaw mechanism located on the distal end of the surgical instrument.

4. The method of claim 1, wherein urging the spinal rod toward the anchoring device is accomplished by rotating a portion of the surgical instrument that is releasably attached to the locking cap to linearly advance the locking cap against the spinal rod.

5. The method of claim 1, wherein securing the spinal rod to the anchoring device involves manipulating the surgical instrument to rotatably lock the locking cap to the anchoring device.

* * * * *